United States Patent [19]
Throckmorton et al.

[11] 3,937,727
[45] Feb. 10, 1976

[54] PROCESS FOR PREPARING N, N-DIMETHYLUREA

[75] Inventors: Peter E. Throckmorton, Worthington; Sari Frey; Dace Grote, both of Columbus, all of Ohio

[73] Assignee: Ashland Oil, Inc., Ashland, Ky.

[22] Filed: July 5, 1974

[21] Appl. No.: 485,835

[52] U.S. Cl. .............................. 260/553 R; 44/71
[51] Int. Cl.² ..................................... C07C 127/15
[58] Field of Search ............................... 260/553 R

[56] References Cited
UNITED STATES PATENTS
2,253,528    8/1941    Olin .............................. 260/553 R Primary Examiner—Arthur P. Demers

[57] ABSTRACT

Urea is reacted with at least a onefold molar excess of dimethylamine in a substantially anhydrous system under pressure and temperature conditions adapted to produce unsymmetrical dimethylurea in essentially quantitative yields.

6 Claims, No Drawings

PROCESS FOR PREPARING N, N-DIMETHYLUREA

BACKGROUND OF THE INVENTION

1. Field of the Invention

This invention relates to an improvement in a process for indirectly alkylating urea.

2. Description of the Prior Art

In order to appreciate the manner in which the present invention represents a marked improvement over the closest prior art, it warrants considering briefly the usefullness N, N-dimethylurea potentially offers as a chemical intermediate. The indicated utility is that of producing unsymmetrical dimethylhydrazine (UDMH), in turn a versatile intermediate for the preparation of surfactants, insecticides, dyes, monomers, etc.; but the most important current use thereof being in the field of liquid propellants for rockets.

Recently, an alternate method to that of the present commercial practice for producing UDMH involving the hydrogenation of nitrosodimethylamine, has been actively sought. This is so because nitrosodimethylamine has been identified as such a powerful carcinogen that in order to provide absolute protection for plant workers a prohibitively expensive installation would be required. An environmentally acceptable alternate method appearing to have commercial merit resides in the modification of the Scheslakoff process (J. Russ. Phys. Chem. Soc., 37, pgs. 1–7, 1905) wherein N, N-dimethylurea is rearranged in accordance with the Hoffman mechanism. As is characteristic of such type rearrangement reactions, optimum yields of product are substantially less than quantitative.

It has hitherto been proposed to prepare N, N-dimethylurea by reacting dimethylamine sulphate with urea in an aqueous system capable of effecting solubilization of the urea. Besides recovery problems, the method suffers because the optimum yields attainable are reportedly in the order of only about half of theoretical. Notwithstanding that the indicated reactants are readily available and relatively inexpensive, the commercial attractiveness of the modified Scheslakoff process for preparing UDMH depends largely on realizing a highly efficient method for preparing N, N-dimethylurea. Accordingly, the foremost objective of the instant invention is to provide such a method.

SUMMARY OF THE INVENTION

In accordance with the broadest aspect of the present invention urea is reacted with dimethylamine in a substantially anhydrous system to provide N, N-dimethylurea. Beyond the essential anhydrous feature of the process, a critical requirement is that of maintaining the reactants in an essentially liquified form during the course of reaction without resorting to the use of added solvent media. The stated requirement is realized through the use of the combination of an appropriately selected elevated reaction temperature and at least a onefold molar excess of dimethylamine based on the extant amount of urea available at any time for reaction. The preferred pressure conditions contemplated correspond to the particular vapor pressure of the dimethylamine at the selected operating temperature.

The salient advantage of the process of this invention over the prior art is that an essentially quantitative yield of N, N-dimethylurea is provided. Another advantage is that the product conversion rates experienced are excellent. Additionally, the product recovery feature of the process together with product purity realized renders the overall process highly efficient.

DESCRIPTION OF THE PREFERRED EMBODIMENTS

The reaction between urea and dimethylamine in accordance with the present invention proceeds, from all indications, by the urea first equilibrating into ammonia and cyanic acid, whereupon the latter reacts with dimethylamine to yield the unsymmetrical dimethylurea. This proposed reaction scheme serves to account for the reported poor results obtained pursuant to the prior art practices. Thus where there is water present, a competing reaction is prone to occur whereby water reacts with cyanic acid to yield carbon dioxide and ammonia. The absence of water in the instant process, therefore, primarily accounts for the essentially quantitative yields being obtained. As implied in the foregoing discussion, water does not poison the reaction in the usual sense. In order to anticipate the extent of water build-up that can be tolerated, which build-up would indubitably occur in constant recycling of unreacted dimethylamine in a commercial operation, it was found that amounts up to 5% based on the weight of the amine reactant had no preceptible effect upon yield or conversion rates. A quantum of water, however, in excess of about 10% based on the amine reactant can be expected to have a progressively noticeable adverse effect on yield. Therefore, in the context of the present invention the phrase "substantially anhydrous system" connotes those reaction systems wherein the amount of water present does not exceed about 10% of the weight of the dimethylamine.

In light of the nature of the reaction between urea and the dimethylamine, the presence of a polar solvent which at the same time serves as a mutual solvent for the reactants is paramount. In the practice of the present invention, the excess of dimethylamine contemplated serve as the required polar solvent. Of course, in this instance the use of an elevated temperature is necessary in order to effect the requisite solubilization of the urea which is much less soluble in dimethylamine than in water. Further discussion with respect to the influence of temperature will be more appropriately set forth hereinbelow. The minimum amount of dimethylamine applicable should be at least a 100% molar excess based on the maximum amount of urea available at any time during the reaction. Substantially larger excesses of dimethylurea can obviously be used but no practical advantages are provided by employing more than three moles of the amine to urea. The optimum ratio noted has been that of 2.5 moles of the amine to urea. Accordingly, the preferred molar ratio of dimethylamine to urea is from about 2.5:1::3.0:1, respectively.

The applicable temperature range for conducting the reaction as aforesaid is between about 110° and 150° C. The lower temperature limit specified permits a substantially homogenous liquid system when employing the least excess of dimethylamine contemplated. The applicable maximum temperature is governed by the critical temperature of the dimethylamine. But from a practical standpoint it is desirable to limit the upper temperature to somewhat less than said critical temperature; namely, in the order of about 150° C. The preferred temperature range is from 125° to 130° C.

In view of the low boiling point of dimethylamine, a closed reaction system for carrying out the present invention is indicated. The applicable pressure conditions are autogenic and for the most part depend upon the operating reaction temperature. During the course of the reaction, however, ammonia is produced in amount which can cause the pressure to rise considerably. Beyond resulting in the need for expensive high pressure equipment, the presence of ammonia adversely affects the conversion rate insofar as the underlying reaction is an equilibrium one. Consequently, the preferred procedure is to vent the reaction system periodically in order to allow by-product ammonia to escape. In following this procedure the system should be vented for only the time needed for the pressure to be lowered to that of dimethylamine at the observed reaction temperature.

As indicated hereinabove, the practice of the present invention permits the realization of essentially theoretical yield of the unsymmetrical dimethylurea. Apart from yield, the conversion values attainable are excellent. Specifically in this regard, employing the preferred conditions noted above in a commercial type reactor, a conversion of an excess of 90 percent in less than an hour can be expected. In light of this feature, the process is ideally suited for batch operations. This is not to say, however, that the process can not be conducted continuously; but as inferred this may not be economically justified.

Another important advantageous aspect of the present process resides in the fact that the dimethylurea precipitates from the reaction mixture in a crystalline mass upon formation. Thus upon completion of the reaction, the unreacted dimethylamine can be readily recovered for recycling purposes and thereupon the crystalline product can be slurried with water and conveniently pumped or otherwise discharged from the reactor. The product can be further purified by a conventional crystallization procedure if desired although reactor purity of in excess of about 95% can be readily achieved.

In order to illustrate to those skilled in the art the manner in which the present invention can be implemented, the following working examples are set forth. The primary purpose of the first working example is to illustrate the effect of certain variables on the process, all as discussed hereinabove. The succeeding example represents the best mode contemplated for carrying out the invention. It is to be understood that these examples are provided solely by way of illustration and accordingly, any enumeration of details set forth therein is not to be interpreted as limiting the invention except as such limitations appear in the appended claims. All parts are parts by weight unless otherwise indicated.

EXAMPLE I

In carrying out the runs of this example a 316 SS Parr bomb reactor was used having a capacity of about 2 liters. The amount of reactants charged in each instance totalled from 150 to 575 g. A uniform charging procedure was observed consisting of first chilling the bomb to approximately −5° to 0° C. and thereupon adding the urea followed by the addition of liquid dimethylamine at −5° to 0° C. The reaction mixture was briefly stirred and the reactor sealed. Heating was then applied to achieve the selected operating temperature, and the reaction was stirred continously. The combining ratio of reactants observed in each run together with processing parameters applicable therein are noted in Table I set forth hereinbelow. The conversion values given are based on the crude product, a determination of which was afforded by means of a melting point phase diagram of mixtures of authentic N, N-dimethylurea and pure crystalline urea. The yield in each instance was quantitative. The indicated pressure of Runs 2 and 4 was maintained by venting the reactor periodically whereas autogenic pressure prevailed in the other runs.

TABLE I

| Run | DMA/Urea | Time(Hrs.) | Temp. °C | Press. | Conversion |
|---|---|---|---|---|---|
| 1 | 2.7 | 1.5 | 130 | 350 | 65 |
| 2 | 2.5 | 2.67 | 124 | 460 | 78 |
| 3 | 2.5 | 1.5 | 120 | 500 | 75 |
| 4 | 2.5 | 1.25 | 124 | 460 | 70 |
| 5 | 2.5 | 3.0 | 90 | 195 | 0 |
| 6 | 2.5 | 1.5 | 70 | 150 | 0 |
| 7 | 2.1 | 1.5 | 110 | 420 | 70 |
| 8 | 2.1 | 1.75 | 105 | 210 | 55 |

EXAMPLE II

In the run of this example a 30 gallon stainless steel pressure reactor was used. The reactor was equipped with a stirrer, cooling coils, electric heating elements, vacuum means and condenser. Crystalline urea in the amount of 45.3 lbs. was first charged to the reactor. The reactor was then sealed and thereupon 84.8 lbs. of dimethylamine were added. Stirring was commenced when the fluidity of the reactor contents permitted. With continued stirring the temperature was raised to 127° C. During the course of the reaction the ammonia produced was vented in order to maintain the pressure at 450 psig. After 45 minutes reaction time, ammonia formation had practically subsided indicating the completion of the reaction. The reactor was then cooled and the excess dimethylamine vented and condensed. Residual amine was finally drawn off under vacuum following which 70 lbs. of water were added, and an aqueous slurry of 135 lbs. was discharged. Analysis of the crystalline product by chromatography indicated it to be free of urea or biuret. The product exhibited a melting point range of 180°–185° C. indicating that essentially complete conversion had been achieved. After recrystallization from water, the product melted at 181.5°–183.5° C. The recrystallized product was shown by infrared and magnetic resonance analysis to be 100 percent pure.

What is claimed is:

1. A process for the preparation of N, N-dimethylurea which comprises reacting dimethylamine and urea neat in a molar ratio of not less than 2:1, respectively, under autogenous pressure and substantially anhydrous conditions at a temperature of from 110° to 150° C.

2. A process in accordance with claim 1 wherein the reaction temperature is from 125° to 130° C.

3. A process in accordance with claim 2 wherein the mole ratio of dimethylamine to urea is from about 2.5:1::3.0:1, respectively.

4. A process in accordance with claim 3 wherein the mole ratio of dimethylamine to urea is 2.5:1, respectively.

5. A process in accordance with claim 4 wherein the reaction system is maintained at about 450 psig.

6. A process in accordance with claim 5 wherein the reaction is carried out until the evolution of ammonia substantially completely subsides and thereupon cooling and venting the reaction mixture to effect the removal of unreacted dimethylamine.

* * * * *